(12) United States Patent
Justis et al.

(10) Patent No.: US 8,211,146 B2
(45) Date of Patent: Jul. 3, 2012

(54) IMPLANTABLE DEVICE AND METHOD OF FORMING

(75) Inventors: Jeffrey R. Justis, Memphis, TN (US); Jonathan M. Dewey, Sunnyvale, CA (US); Henry Keith Bonin, Jr., Memphis, TN (US); Christopher M. Patterson, Memphis, TN (US); Dimitri K. Protopsaltis, Memphis, TN (US)

(73) Assignee: Warsaw Orthopedic, Warsaw, IN (US)

( * ) Notice: Subject to any disclaimer, the term of this patent is extended or adjusted under 35 U.S.C. 154(b) by 681 days.

(21) Appl. No.: 12/167,457

(22) Filed: Jul. 3, 2008

(65) Prior Publication Data
US 2010/0004685 A1 Jan. 7, 2010

(51) Int. Cl.
*A61B 17/70* (2006.01)
(52) U.S. Cl. .................................................. 606/246
(58) Field of Classification Search .................. 606/279, 606/257, 254, 261, 60, 246, 907, 910, 260, 606/278, 263
See application file for complete search history.

(56) References Cited

U.S. PATENT DOCUMENTS

| 7,621,912 | B2 * | 11/2009 | Harms et al. ............... 606/59 |
| 7,785,350 | B2 * | 8/2010 | Eckhardt et al. ............ 606/254 |
| 7,942,905 | B2 * | 5/2011 | Lim et al. .................. 606/257 |
| 7,951,170 | B2 * | 5/2011 | Jackson ..................... 606/257 |
| 2004/0049189 | A1 | 3/2004 | Le Couedic et al. |
| 2005/0177156 | A1 | 8/2005 | Timm et al. |
| 2005/0261685 | A1 * | 11/2005 | Fortin et al. ................ 606/61 |
| 2005/0277922 | A1 | 12/2005 | Trieu et al. |
| 2007/0190230 | A1 | 8/2007 | Trieu et al. |
| 2007/0225710 | A1 * | 9/2007 | Jahng et al. ................ 606/61 |
| 2007/0270837 | A1 | 11/2007 | Eckhardt et al. |
| 2009/0005817 | A1 * | 1/2009 | Friedrich et al. ........... 606/246 |
| 2009/0093845 | A1 * | 4/2009 | Hestad et al. .............. 606/254 |
| 2009/0118767 | A1 * | 5/2009 | Hestad et al. .............. 606/279 |
| 2009/0131981 | A1 * | 5/2009 | White ....................... 606/246 |

FOREIGN PATENT DOCUMENTS
WO 2005110257 A1 11/2005
* cited by examiner

*Primary Examiner* — Pedro Philogene

(57) ABSTRACT

An implantable device includes a first arm member, a second arm member, a compressible member disposed between and coupled to the first arm member and the second arm member, and a tensioning member coupled to the first arm member and the second arm member. Wherein upon moving the first arm member toward the second arm member the tensioning member translates within the first arm member.

13 Claims, 11 Drawing Sheets

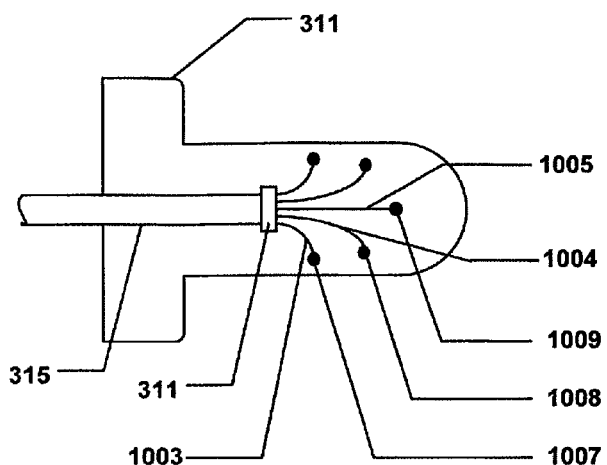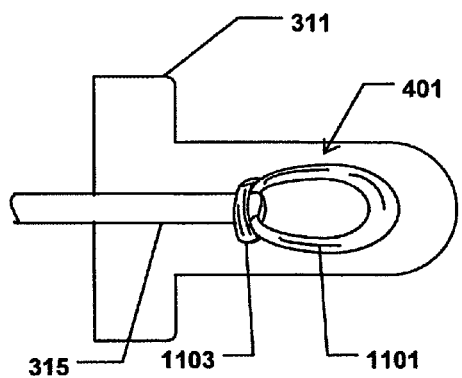
FIG. 10  FIG. 11
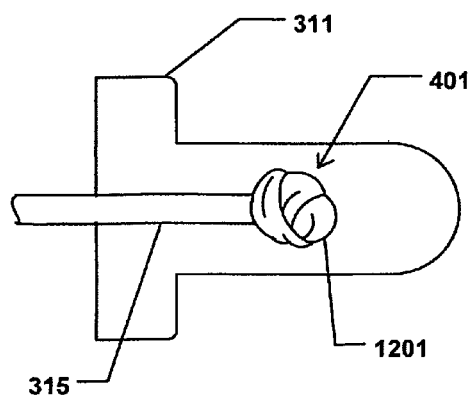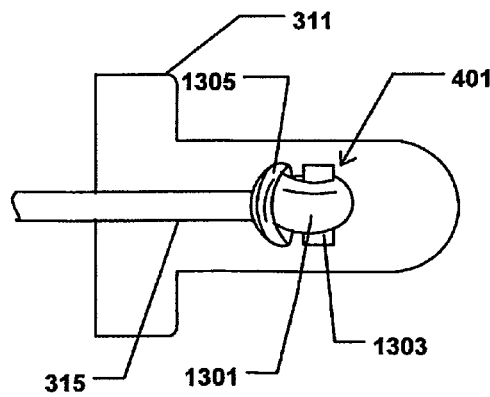
FIG. 12  FIG. 13

IMPLANTABLE DEVICE AND METHOD OF FORMING

BACKGROUND

1. Field of the Disclosure

The following is directed to an implantable device, and more particularly directed to an implantable device for correction or repair of the spine.

2. Description of the Related Art

There are a variety of different spinal conditions, such as scoliosis, as well as others, which may be cured or mitigated by implantation of certain devices. Such devices can include articles and mechanisms useful for repairing damaged portions of the spine, stabilizing portions of the spine, or changing the position of the spine to a more healthy state. For example, rod and anchor systems are commonly employed when portions of the spine need to be realigned, such as in patients with abnormal curvatures, wherein the rod provides rigid support for urging the spine to a more healthy position.

Other implants, such as plates, tethers, wires, and cables can be implanted along the spinal column between two or more anchors engaged within the spine for stabilization and repair. However, such implants typically provide a rigid construct that resist movement of the spine in response to spinal loading or movement by the patient. Still, some other implants have partial flexibility to permit at least limited spinal motion.

While a variety of implants exist that provide certain spinal stabilization options, there remains a need for improved devices that properly stabilize the spine while also accommodating motion.

SUMMARY

According to one aspect, an implantable device includes a first arm member, a second arm member, a compressible member disposed between and coupled to the first arm member and the second arm member. The device further includes a sleeve bonded to the first arm member and extending into an interior of the first arm member, wherein the sleeve has an interior surface defining a passage and tensioning member coupled to the first arm member and the second arm member, and a portion of the tensioning member extending through the passage wherein upon moving the first arm member toward the second arm member the tensioning member translates within the first arm member. The tensioning member can extend through an interior of the compressible member, and can be fixably connected to the second arm member, such that the relative position of the members are fixed relative to one another.

The sleeve can have a portion that is exterior to the first arm member and in direct contact with the compressible member. The sleeve can further include a portion extending into an interior of the first arm member. The sleeve can include an opening adjacent to an interface between the first arm member and the compressible member, for the tensioning member to extend through.

The tensioning member can further include an end member coupled to a terminating end of the tensioning member and embedded within the first arm member. Notably, the end member is integrally bonded to the material of the first arm member. The end member can have various shapes, such as a cylindrical, rectangular, spherical or irregular shape. The end member can further include a protrusion or flange. Moreover, the end member can have a diameter greater than a diameter of the tensioning member. In other instances, the tensioning member can include a series of individual wires braided together to form a braided wire, and the braided wire is tied to the end member.

The tensioning member comprises a metal or metal alloy including for example, cobalt, chromium, molybdenum, aluminum, titanium, iron, and nickel and a combination thereof. The tensioning member comprises a braided metal wire. Alternatively, the tensioning member can include a polymer, such as polyurethane, polyolefin, polyether, polyester, and polycarbonate. In particular the tensioning member can include a polyether such as of polyetherketone (PEK), polyetheretherketone (PEEK), polyetherketoneketone (PEKK), polyaryletherketone (PAEK). The tensioning member can include a reinforced polymer, and in some instances may include a PEEK wire.

The end member can be housed within the sleeve and configured to slideably engage an inner surface of the sleeve. The sleeve can include a bearing surface that includes a polymer. Some suitable polymers can include a fluoropolymer such as polytetrafluoroethylene (PTFE).

Furthermore, the sleeve may include a flange configured to abut a portion of the end member and limits the movement of the end member. The sleeve can have multiple components, including a neck portion configured for translation of the tensioning member therein and having a flange extending at a proximal end adjacent to an interface between the first arm member and the compressible member. The sleeve can include a bearing surface that is angled arcuate and configured to engage a portion of the tensioning member.

The device can further include a biasing member within the first arm member, and more particularly housed within a portion of the sleeve and is configured to bias an end member. The biasing member can be coupled to a portion of the tensioning member against a surface of the sleeve. The biasing member can be a biasing sleeve substantially surrounding a portion of the tensioning member adjacent to the end member.

The first arm member or second arm member can include a polymer such as polyurethane, polyolefin, polyether, polyester, and polycarbonate. Suitable polyether materials can include polyetherketone (PEK), polyetheretherketone (PEEK), polyetherketoneketone (PEKK), polyaryletherketone (PAEK). The compressible can include an organic material such as a natural material or a polymer material. For example, the compressible member can include an elastomer.

According to another aspect, an implantable device is described that includes a first arm member, a second arm member, and a compressible member disposed between and coupled to the first arm member and the second arm member. The device further includes a sleeve positioned within an interior of and bonded to the first arm member, wherein the sleeve has an opening, and a tensioning member coupled to the second arm member, extending through the compressible member, the opening of the sleeve, and into the interior of the first arm member.

In one particular condition a majority of the sleeve is embedded within first arm member, and is substantially centered in the first arm member along a longitudinal axis of the first arm member. The sleeve can include the same material as the material of the first arm member, or a different material than the material of the first arm member. In fact, the sleeve can use a variety of materials, such ceramics, metals, and polymers. Notably, in some cases, the sleeve has a hardness that is less than the hardness of the first arm member, and may also have a hardness that is greater than the hardness of the tensioning member.

In another aspect, an implantable device includes a first arm member, a second arm member, and a compressible member disposed between and coupled to the first arm member and the second arm member. The device further includes a tensioning member extending through an interior of the compressible member and into an interior of the first arm member, and an end member coupled to the tensioning member, wherein the end member is further integrally bonded with the material of the arm member and embedded within an interior of the arm member such that it is spaced apart from exterior surfaces of the arm member.

In certain instances, the end member can include a grouping of splayed wires, or alternatively a knot of wire. The end member can include multiple components, such as a body portion coupled to the knot of wire. Moreover, the end member can be made of the same material as the material of the tensioning member, or alternatively, a material different than the material of the tensioning member. Suitable materials for the end member may include polymers, such as a polyether material. For example, some polyether materials include polyetherketone (PEK), polyetheretherketone (PEEK), polyetherketoneketone (PEKK), polyaryletherketone (PAEK). Still, the end member may be made of a metal or metal alloy.

In one particular example, the end member is embedded within the interior of the first arm member at a depth that is at least about 25% of the total length of the first arm member. Other examples use a different depth, such as at least about 50% of the total length of the first arm member, and particularly within a range between about 50% and about 90% of the total length of the first arm member.

In accordance with another aspect, a method of forming an implantable device is described that includes forming an end member coupled to a tensioning member, placing the tensioning member having the end member within a forming machine, and forming a polymer material around the end member and a portion of the tensioning member to form an arm member, wherein the end member is embedded within the polymer material after forming.

The process of forming the end member can include tying a terminating end of the tensioning member to an end member body, which may be facilitated in certain embodiments using a tensioning member made of a plurality of individual wires. The process can further include manipulating a portion of the individual wires to form a structure selected from the group of structures consisting of a knot, a braid, a loop, and a twist.

The process may include in particular placing a portion of the tensioning member in a sleeve to form a sub-assembly. The process may then include centering the sub-assembly within the forming machine, such that a portion of the sleeve is engaged with a portion of the forming machine to center the sub-assembly within a forming chamber of the forming machine. As described herein, the sleeve can include an upper portion configured to house the end member, and a neck portion configured to house a portion of the tensioning member.

The process can also include placing a biasing member within the sleeve and substantially surrounding a portion of the tensioning member. Additionally, the forming a polymer can include a process selected from the group of processes including injection molding and compression molding. In one particular example, the forming process is compression molding and the polymer material is a polyether, such as PEEK.

BRIEF DESCRIPTION OF THE DRAWINGS

The present disclosure may be better understood, and its numerous features and advantages made apparent to those skilled in the art by referencing the accompanying drawings.

FIG. 10 includes a cross-sectional illustration of a portion of an implantable device in accordance with an embodiment.

FIG. 11 includes a cross-sectional illustration of a portion of an implantable device in accordance with an embodiment.

FIG. 12 includes a cross-sectional illustration of a portion of an implantable device in accordance with an embodiment.

FIG. 13 includes a cross-sectional illustration of a portion of an implantable device in accordance with an embodiment.

The use of the same reference symbols in different drawings indicates similar or identical items.

DETAILED DESCRIPTION

Figure 1:
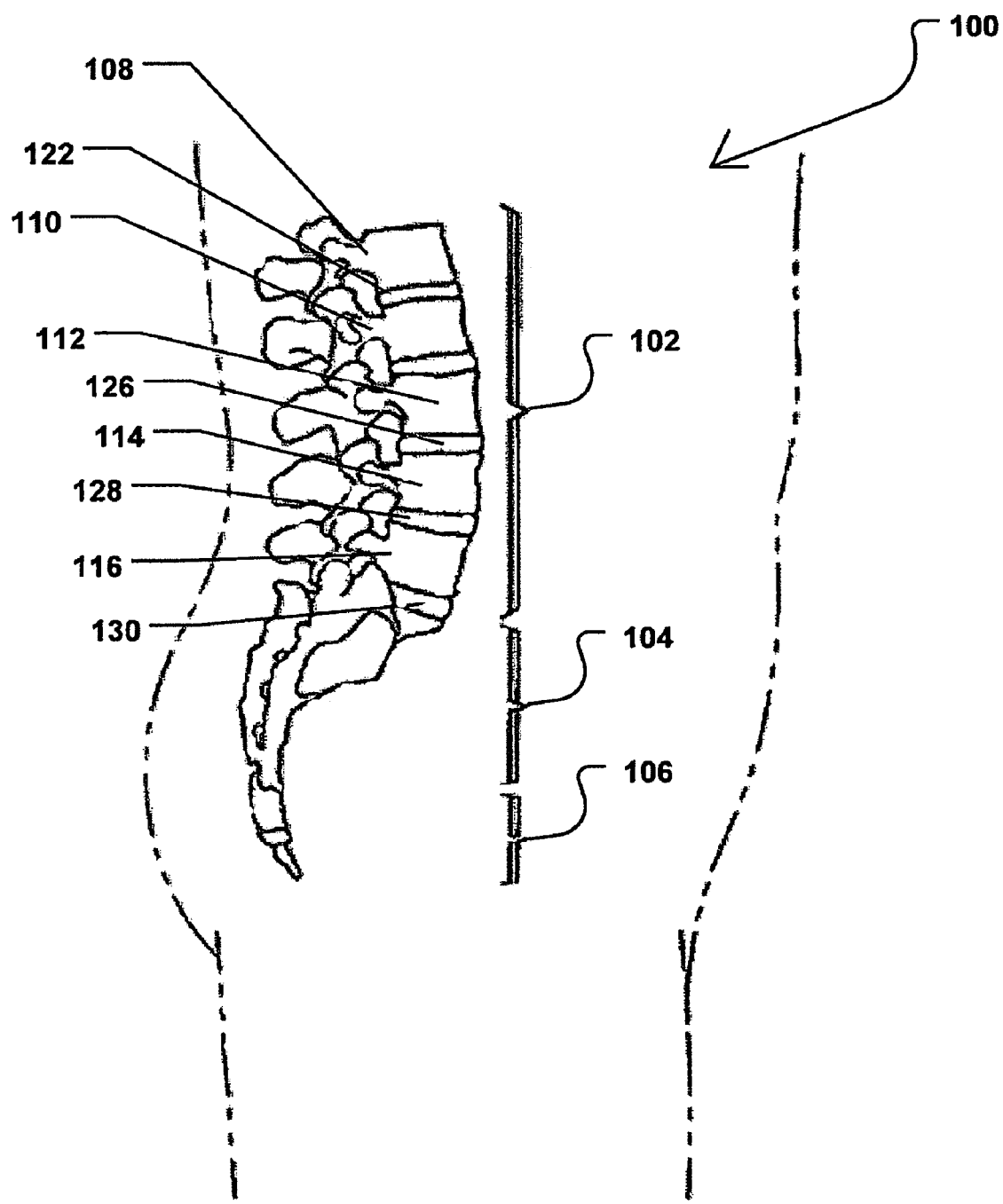
FIG. 1 includes a lateral view of a portion of a vertebral column.

The following introductory figures provide illustrations of anatomy relevant to the use of the implantable device described herein. Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if portions of the spine are diseased, degenerated, or damaged or if one of the zygapophyseal joints is diseased, degenerated or damaged, that region may be at least partially treated with a device according to one or more of the embodiments described herein.

Figure 2:
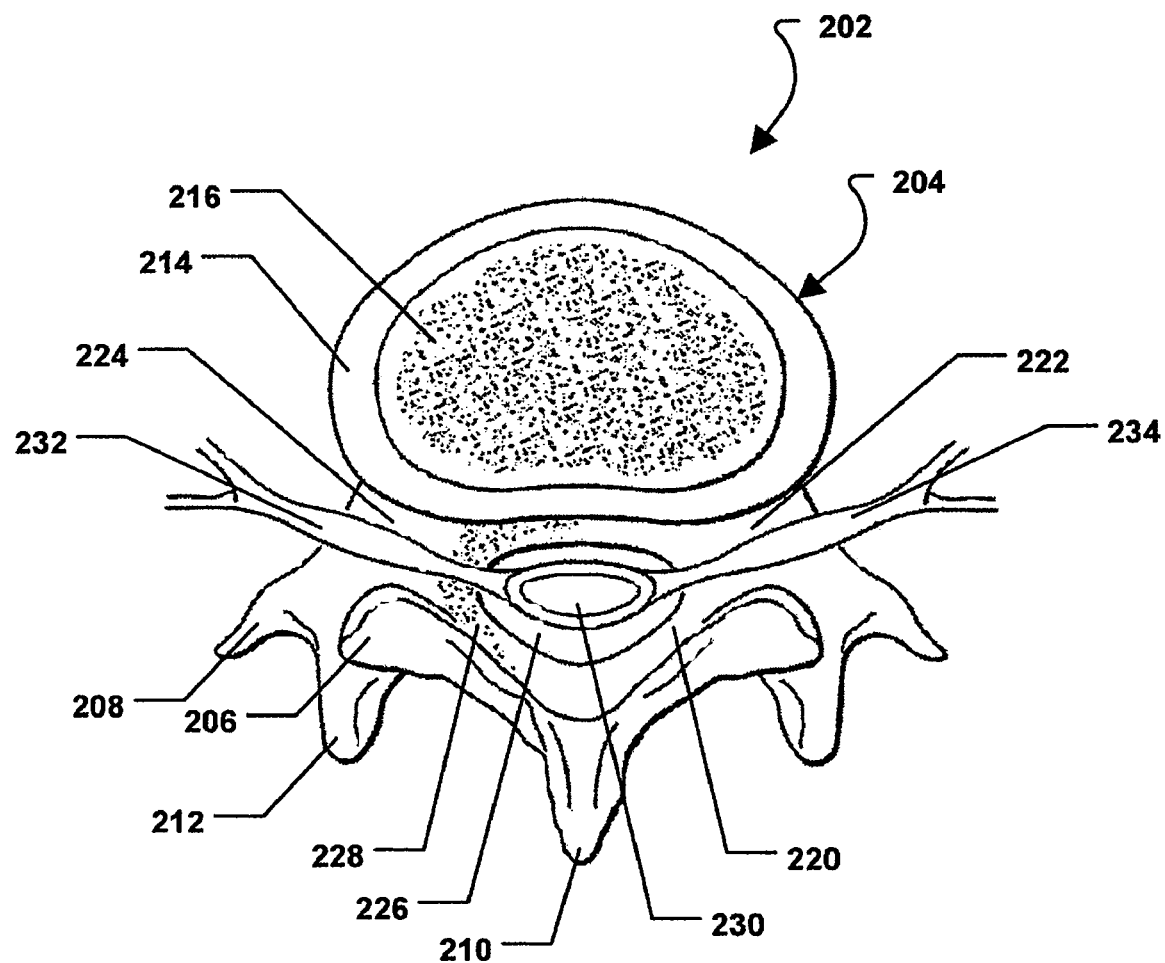
FIG. 2 includes a top-plan view of a vertebrae.

Referring to FIG. 2, a top plan view of a vertebra is illustrated. As illustrated, the vertebral body 204 of the inferior vertebra 202 includes a cortical rim 214 composed of cortical bone. In addition, the vertebral body 204 includes cancellous bone 216 within the cortical rim 214. The cortical rim 214 is often referred to as the apophyseal rim or apophyseal ring. Further, the cancellous bone 216 is softer than the cortical bone of the cortical rim 214.

As illustrated in FIG. 2, the inferior vertebra 202 further includes a first pedicle 222, a second pedicle 224, a first lamina 220, and a second lamina 228. Further, a vertebral foramen 226 is established within the inferior vertebra 202. A spinal cord 230 passes through the vertebral foramen 226, and a first nerve root 232 and a second nerve root 234 extend from the spinal cord 230. Moreover, each vertebra includes a superior articular process 206, a transverse process 208, a spinous process 210, and an inferior articular process 212.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2. The first and second cervical vertebrae are structurally different than the rest of the vertebrae in order to support a skull.

Figure 3:
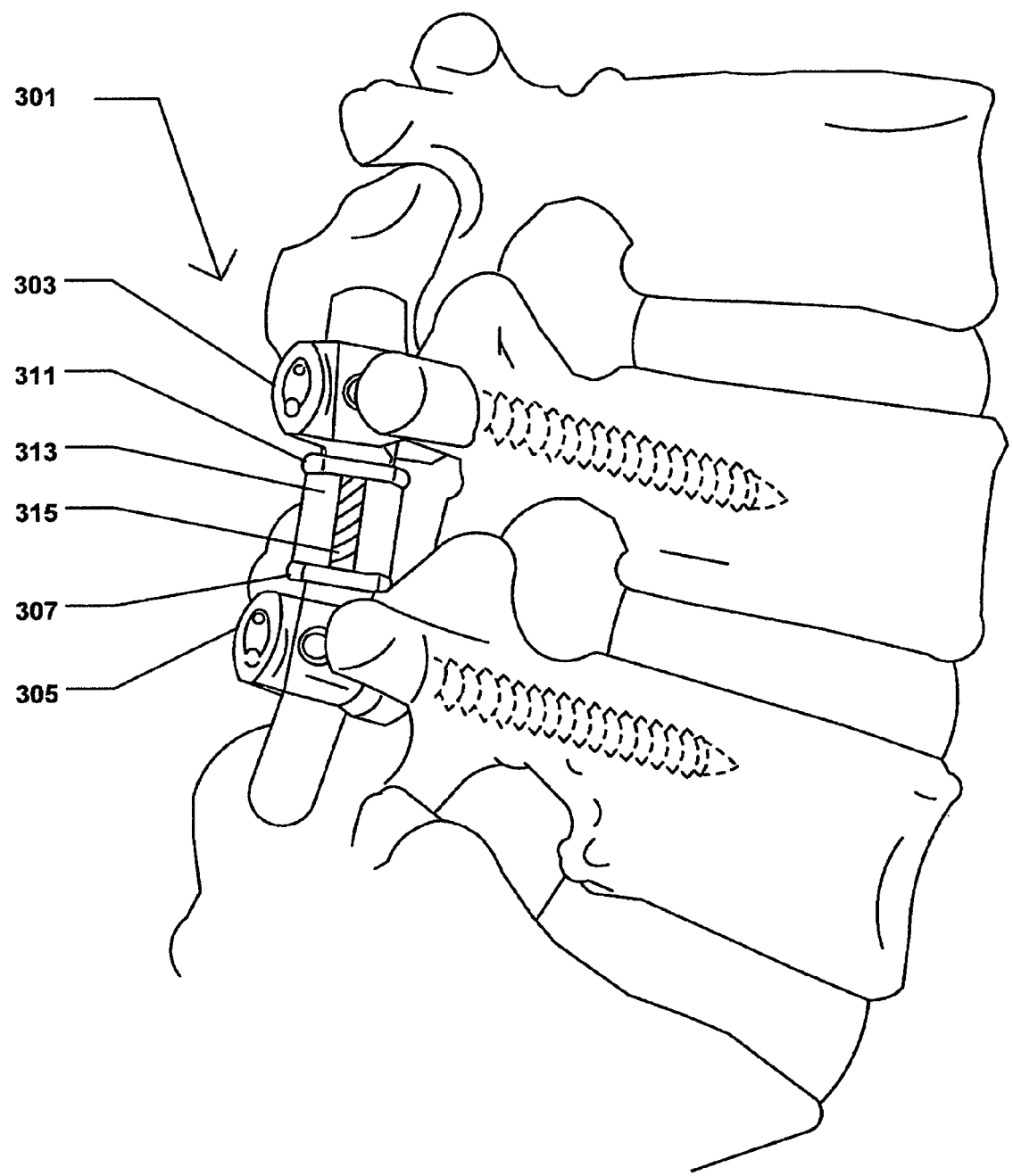
FIG. 3 includes a perspective view of a portion of a vertebral column and an implantable device in accordance with an embodiment.

FIG. 3 illustrates a generalized structure of an implantable device and the orientation in which it can be generally affixed to a portion of a spine. The implantable device of the embodiments herein is used to provide dynamic stabilization to a portion of the spine by preserving motion in three dimensions including extension, flexion, and torsion. In particular, the implantable device 301 has such a design that it allows for dynamic transitioning, thus accommodating various kinds of loads along the portion of the spine while providing suitable stabilization to the spine and avoiding harm to the patient.

As illustrated in FIG. 3, the implantable device 301 includes an arm member 307 that is connected to an anchor 305, and an arm member 311 also connected to an anchor 303 thereby coupling the device 301 to the spine. The device 301 further includes a compressible member 313 disposed between and coupled to the arm members 307 and 311, configured to manage compressive forces placed on the device 301. As further illustrated, the device 301 includes a tensioning member 315 coupled to the arm members 307 and 311, extending through the interior of the compressible member 313, and configured to manage tensioning forces placed on the device 301. While FIG. 3 illustrates a single device 301 coupled to the spine, it will be appreciated that multiple devices may be coupled along the spine depending upon the needs of the patient.

Figure 4:
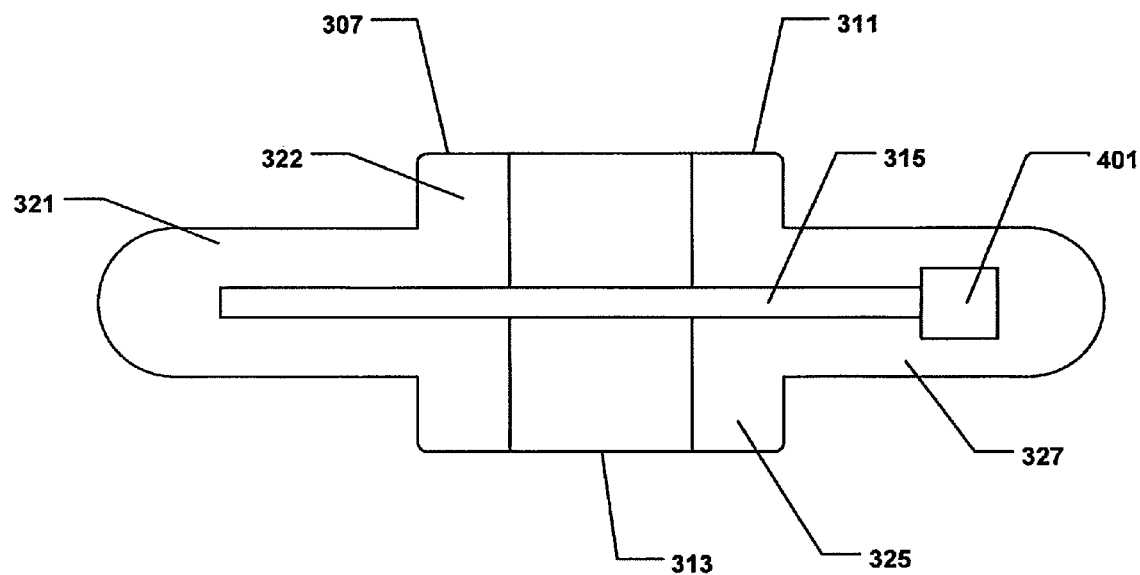
FIG. 4 includes a cross-sectional illustration of an implantable device in accordance with an embodiment.

FIG. 4 includes a cross-sectional illustration of an implantable device in accordance with an embodiment. In particular, FIG. 4 illustrates the design and integration of the components, particularly the tensioning member 315, disposed within the interior of the device. As illustrated, the arm member 307 can include an elongated portion 321 having a flange 322 coupled thereto. The design of the arm member 307 facilitates engagement with an anchor along the elongated portion 321, the flange 322 provides a larger surface 323 for coupling with the compressible member 313.

The arm member 307 can be made of a biocompatible polymer material. For example, some suitable polymer materials include polyurethanes, polyolefins, polyethers, polyesters, and polycarbonates or any combination thereof. In certain embodiments, the arm member 307 is made of a polyether, such as polyetherketone (PEK), polyetheretherketone (PEEK), polyetherketoneketone (PEKK), polyaryletherketone (PAEK). According to one particular embodiment, the arm member 307 is made entirely of PEEK.

As further illustrated in FIG. 4, the compressible member 313 is disposed between and coupled to arm members 307 and 311. The compressible member 313 is configured to manage compressive forces placed on the device generally through its elastic or semi-elastic characteristics. As such, the compressible member 313 can be made of a material having a hardness that is less than the hardness of the arm members 307 and 311. Particularly suitable materials can include, biocompatible gels, polymers, and natural organic materials. In one particular embodiment, the compressible member 313 is made of an elastomer, or visco-elastic material.

As further illustrated in FIG. 4, arm member 311 is coupled to the compressible member 313 opposite the arm member 307. Like arm member 307, arm member 311 has a flange portion 325 that is connected to an elongated portion 327 that is suitable for coupling to an anchor and fixing the device to the spine. In accordance with an embodiment, the arm member 311 can include a polymer material, such as those described in accordance with the description of the arm member 307.

As further illustrated in FIG. 4, the device includes a tensioning member 315 coupled to the arm member 307, extending through the interior of the compressible member 313, and into the interior of the arm member 311. The tensioning member 315 is capable of providing resilience in situations of applied tension to the device, reducing the strain to the other components. Notably, a portion of the tensioning member 315 is hermetically encased within the material of the arm members 307 and 311 thus fixing a portion of the tensioning member 315 within the arm members 307 and 311. Accordingly, in certain embodiments, the tensioning member 315 may not extend along a channel or passage within the arm members 307 and 311, but is integrally bonded to the material of the arm members 307 and 311. In particular instances, the tensioning member 315 is under a compressive load within the interior of the arm members 307 and 311 to rigidly secure the components together.

In accordance with one embodiment, the tensioning member 315 can be made of a metal material or a metal alloy. For example, suitable metals can include cobalt, chromium, molybdenum, aluminum, titanium, iron, and nickel, or any combination thereof. Particularly suitable metal alloys can include cobalt/chrome, or a titanium-containing alloy.

In accordance with another embodiment, the tensioning member 315 can include a biocompatible polymer material. Some suitable polymers can include polyurethane, polyolefin, polyether, polyester, and polycarbonate or any combination thereof. In accordance with one particular embodiment, the tensioning member 315 is a polyether material, for example polyetherketone (PEK), polyetheretherketone (PEEK), polyetherketoneketone (PEKK), polyaryletherketone (PAEK). In one particular embodiment, the tensioning member is made entirely of PEEK.

In such embodiments using a polymer material within the tensioning member 315, such polymer materials may be reinforced by other materials. For example, a suitable reinforced polymer can include a carbon fiber reinforced material such as carbon fiber reinforced PEEK.

Additionally, the tensioning member 315 can be a wire, tether, or other elongated member. Still, in particular embodiments, the tensioning member 315 can include multiple individual wires wound together, such as in the form of a braided member. Moreover, as will be appreciated, the tensioning member 315 can be a braided material incorporating a metal, polymer, or a combination thereof. Certain embodiments utilize a braided material, such as a braided metal wire, especially in embodiments using a polymer material in the arm members 307 and 311, since a polymer material will penetrate the openings and crevices between individual wires during forming, thus improving the bond between the tensioning member 315 and the arm members 307 and 311.

As further illustrated in FIG. 4, the device 301 includes an end member 401 disposed within the arm member 311 and connected to the tensioning member 315. The end member 401 is generally connected to a terminating end of the tensioning member 315 and is embedded within the interior of the arm member 311. Notably, in certain embodiments, the end member 401 is hermetically encased within the arm member 311. In such conditions, the end member 401 is embedded within and surrounded by the material of the arm member 311 such that the end member 401 is not exposed to the external environment, including through any passages, openings, and the like. In fact, in certain embodiments, the arm member 311 is integrally bonded at an atomic level to the material of the arm member 311, such that the arm member 311 and end member 401 form a unitary piece, directly and physically attached to each other fixing the location of the end member within the arm member. Moreover, the end member 401 can be positioned within the interior of the arm member 401 such that it is centered in the arm member and coaxially aligned with a longitudinal axis of the arm member. Such features provide suitable coupling strength between the arm member 311 and tensioning member 315 thus avoiding failure of the tensioning member 315 (e.g., by "pull out" of the tensioning member 315 from the arm member 311) in situations of excessive tension upon the device. Other uses of the end member 401 will become evident throughout the description.

The end member 401 can include a material that is the same as the material of the arm member 311. However, in some instances, the end member 401 can include a material that is different than the material of the arm member 311. Moreover, the end member 401 can further include materials that are the same as or different from those materials used in the tensioning member 315. In certain embodiments, the end member 401 can include a metal material or metal alloy such as those described herein. Metal or metal alloy materials may be particularly useful when the tensioning member 315 also comprises a metal or metal alloy material, providing similar materials for a suitable bond between the end member 401 and the tensioning member 315.

Alternatively, the end member 401 can include a biocompatible polymer material, such as those described herein. As such, in one particular instance, the end member 401 includes a polyether material, such as PEEK or carbon-fiber reinforced PEEK. Use of polymer materials within the end member 401 may be suitable in such embodiments where the tensioning member 315 includes a polymer material facilitating a suitable bond between the members.

As will be appreciated, the end member 401 can include a combination of materials such as metals and polymers, as described herein. In particular, a combination of metal and polymer materials may be suitable when the tensioning member 315 and arm member 311 include different materials, for example, in instances where the tensioning member 315 includes a metal material and the arm member 311 includes a polymer material.

FIGS. 5-14 illustrate various embodiments incorporating different components, and particularly different designs of the end member and tensioning member having certain features or combination of features. In each of the following illustrated embodiments, the end members are hermetically encased with the arm members, such that the end members are surrounded by the material of the arm member, having no exposure to the external environment. Moreover, in each of the following embodiments of FIGS. 5-14 a portion of the tensioning member and end member within the arm member are positioned such that they are substantially centered within the arm member, extending along a longitudinal axis of the arm member and spaced apart from exterior surfaces of the arm member. As will be discussed, certain features of the following embodiments are drawn to the depth at which the end member is placed within the arm member, the shape and surface area of the end member, the orientation of the end member within the arm member, and the use of end members having multiple components. All such features rigidly securing the tensioning member to the arm member.

Figure 5:
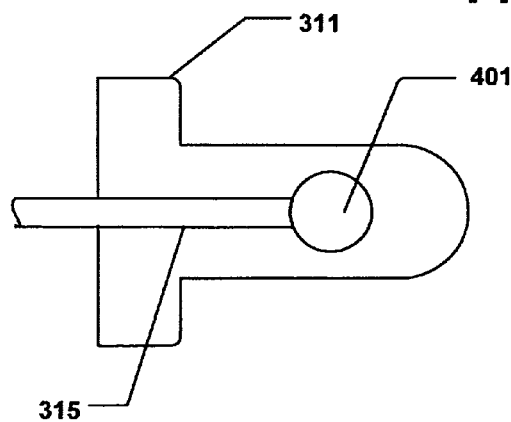
FIG. 5 includes a cross-sectional illustration of a portion of an implantable device in accordance with an embodiment.

Referring to FIG. 5, a cross-sectional illustrational of a portion of an implantable device is provided in accordance with an embodiment. As illustrated, the end member 401 is hermetically encased within the interior of the arm member 311 and coupled to the tensioning member 315. In accordance with a particular embodiment, the end member 401 has a substantially spherical shape. The spherical shape provides a plurality of contact surfaces at various orientations with respect to the material of the arm member 311 thus providing additional surface area for suitable bonding with the material of the arm member. Additionally, the spherical shape avoids localized stress regions akin to shapes with sharp corners.

Figure 6:
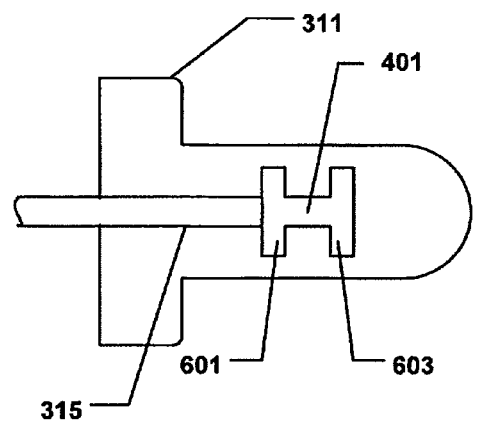
FIG. 6 includes a cross-sectional illustration of a portion of an implantable device in accordance with an embodiment.

FIG. 6 includes a cross-sectional illustration of a portion of an implantable device in accordance with an embodiment. In particular, FIG. 6 illustrates an end member 401 hermetically encased within an interior of the arm member 311 and connected to the tensioning member 315. In particular, the end member 401 generally has a cylindrical shape and includes flanges 601 and 603 spaced apart from each other at opposing ends of the end member 401. The flanges 601 provide additional surface area to bond with the material of the arm member 311 thus suitably securing the end member 401 within the arm member 311. Moreover, the orientation of the flanges 601 and 603 relative to the longitudinal axis of the tensioning member 315 provide suitable resistance from removal of the tensioning member 315 from the arm member 311.

Figure 7:
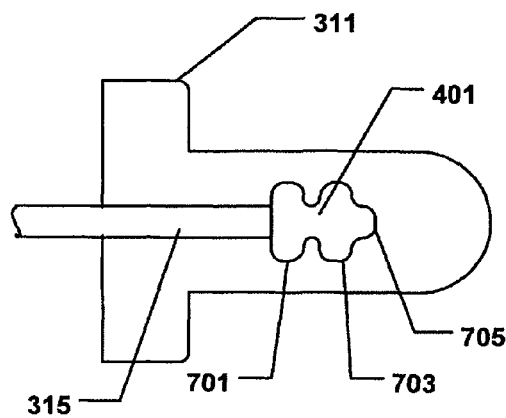
FIG. 7 includes a cross-sectional illustration of a portion of an implantable device in accordance with an embodiment.
Figure 8:
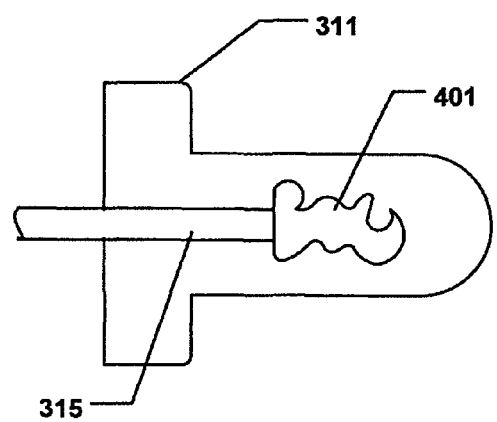
FIG. 8 includes a cross-sectional illustration of a portion of an implantable device in accordance with an embodiment.

FIG. 7 includes a cross-sectional illustration of a portion of an implantable device in accordance with an embodiment. In particular, FIG. 4 illustrates an end member 401 hermetically encased within the arm member 311 and connected to the tensioning member 315. As illustrated, and in accordance with a particular embodiment, the end member 401 can include a plurality of protrusions 701, 703, and 705 extending from an outer surface of the end member 401. The protrusions 701, 703, and 705 increase the surface area of the end member and improve the bond between the end member 401 and the arm member 311. While illustrated as having generally rounded shapes, the protrusions 701, 703 and 705 can include other geometries such as rectangular, hexagonal, triangular, or more irregular shapes, for example a helical protrusion extending around the circumference of the end member. For example, referring briefly to FIG. 8, a cross-sectional illustration of a portion of an implantable device incorporating an alternatively shaped end member 401 is provided. In particular, the end member 401 has an irregular shape including a combination of protrusions, indentations, corners, and even a hooked portion.

Figure 9:
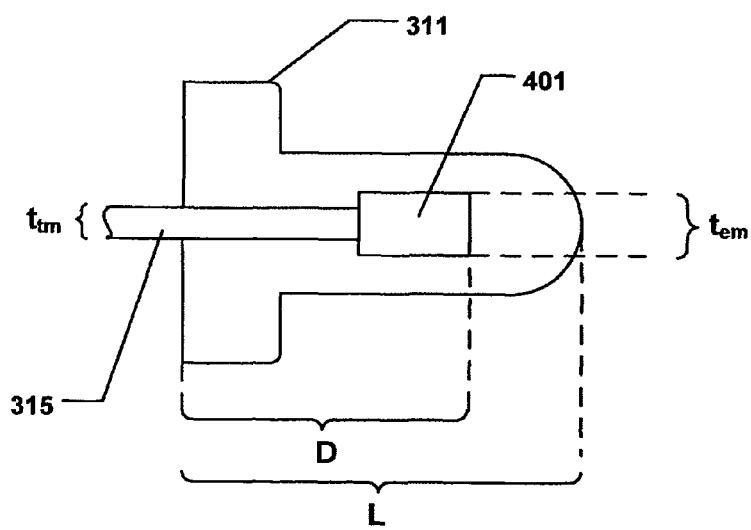
FIG. 9 includes a cross-sectional illustration of a portion of an implantable device in accordance with an embodiment.

FIG. 9 includes a cross-sectional illustration of a portion of an implantable device in accordance with an embodiment. As illustrated, an end member 401 is hermetically encased within an interior of the arm member 311 and connected to the tensioning member 315. The end member 401 has a generally rectangular cross-section and may have a generally cube shape or alternatively a cylindrical shape. However, in accordance with one particular embodiment, the end member 401 has a thickness ($t_{em}$) that is greater than the thickness of the tensioning member ($t_{tm}$) 315. In accordance with a particular embodiment, the thickness of the end member ($t_{em}$) 401 is greater than the thickness of the tensioning member ($t_{tm}$) 315 by at least 5% of the thickness of the tensioning member ($t_{tm}$) 315. Other embodiments may utilize a greater difference, such as at least about 10%, about 15%, about 25%, or even about 50% greater. Still, the thickness of the end member ($t_{em}$) 401 may be limited within a range between about 10% and 50% greater in thickness then the thickness of the tensioning member 315 ($t_{tm}$). On average, the thickness of the end member ($t_{tm}$) 401 is within a range between about 2 mm and about 10 mm. As will be appreciated, in such embodiments utilizing a cylindrical end member 401 the diameter of the end member 401 can be greater than the diameter of the tensioning member 315 as described with relation to the thickness above. It has been discovered that such dimensions facilitate integral bonding of the end member with the material of the arm member and provide resilience from "pull out" of the tensioning member from the arm member in situation of excessive stress.

Additionally, the end member 401 can be embedded within the arm member 311 at a certain depth (D) such that the end member 401 and tensioning member 315 are suitably bonded within the arm member 311. In accordance with a particular embodiment, the end member is embedded within the interior of the arm member 311 at a depth (D), measured from a distal end of the end member to a front face of the arm member 311 as illustrated in FIG. 9, of at least about 25% of the total length (L) of the arm member 311. In more particular embodiments, the end member 401 may be embedded at a greater depth, such as at least about 35%, about 40%, or even at least about 50% of the total length of the arm member 311. In accordance with one particular embodiment, the arm member 401 is embedded within the interior of the arm member 311 at a depth (D) within a range between about 50% and 90% of the total length (L) of the arm member 311. Notably, the end member 401 does not extend to the end of the arm member 311 such that it is embedded within and substantially surrounded by the material of the arm member 311, providing a suitable bond between the members.

On average, the end member 401 is provided within the arm member 311 at a minimum depth of at least about 2 mm, at least about 4 mm or even at least about 6 mm. In accordance with one particular embodiment, the end member 401 is embedded within the arm member to a depth within a range between about 8 mm to about 20 mm.

FIG. 10 includes a cross-sectional illustration of a portion of an implantable device in accordance with an embodiment.

In particular, the end member 401 comprises a series of splayed individual wires 1003, 1004, and 1005 (1003-1005) that are individually bonded to the arm member 311 and hermetically encased within the interior of the arm member 311 and coupled to the tensioning member 315. In accordance with a particular embodiment, the end member 401 includes a collar 1001 connected to each of the wires 1003-1005 and further connected to the tensioning member 315. As illustrated, each of the individually splayed wires 1003-1005 include enlarged features 1007, 1008, and 1009 (1007-1009) at the ends. The enlarged features can include beads, knots, or other such features. The splayed wires 1003-1005 can be arranged in a random arrangement, or alternatively may be patterned, and extend through a portion of the arm member 315 to provide greater surface area and bonding at different depths to increase the coupling bond strength between the tensioning member 315 and the arm member 311. Notably, such embodiments utilizing the splayed wires 1003-1005 may be particularly suited to embodiments using a tensioning member 315 made of multiple wires, for example a braided member.

FIG. 11 includes a cross-sectional illustration of a portion of an implantable device in accordance with an embodiment. In particular, FIG. 11 illustrates an end member 401 including a loop 1101 of material. In accordance with a particular embodiment, the loop 1101 of material can include a loop of individual wires extending from the end of the tensioning member 315. Moreover, in accordance with another particular embodiment, the end member 401 can include a twist 1103 of material which may be particularly suitable for coupling and retaining the shape of the loop 1101 of material. Generally, such shapes are suitable for increasing the surface area of the end member 401 and improving the bond between the end member 401 and arm member 311. In certain embodiments, the end member 401 can have pores, for example millimeter or micron sized pores within the surface of the material, such that upon forming, the material of the arm member 311 flows into the pores thus improving the bonding between the end member 401 and the arm member 311. In particular, end members 401 utilizing a polymer material can have such pores.

FIG. 12 includes a cross-sectional illustration of a portion of an implantable device in accordance with another embodiment. As illustrated in FIG. 12, the end member 401 includes a knot 1201 of material bonded to and hermetically encased within the interior of the arm member 311. The knot 1201 may be formed by tying an end of the tensioning member 315 on itself to create a region of increased surface area. Additionally, the knot 1201 may also have pores and openings, through which the material of the arm member 311 can flow when using certain forming processes, such as a compression molding technique. An end member 401 made of a knot 1201 may be particularly useful when the tensioning member 315 is a braided member including a plurality of individual wires.

Figure 14:
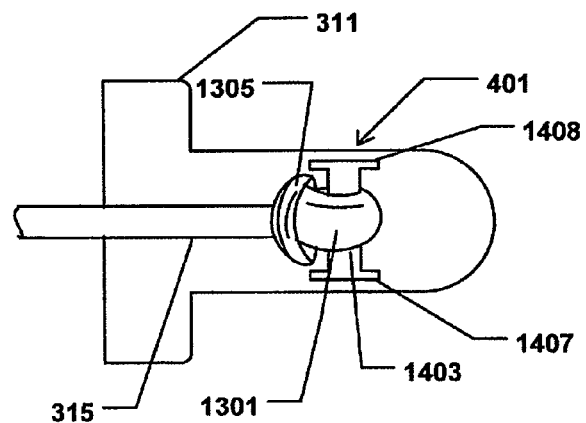
FIG. 14 includes a cross-sectional illustration of a portion of an implantable device in accordance with an embodiment.

FIGS. 13 and 14 illustrate end members having multiple components, including for example, a body member portion and a fastening portion. FIG. 13 includes a cross-sectional illustration of a portion of an implantable device in accordance with an embodiment. The end member 401 includes a body member portion 1303 connected to a fastening portion that connects the body member portion 1303 and the tensioning member 315. As illustrated, the fastening portion includes a loop 1301 of material that is further connected to a twist 1305 of material. In particular, the loop 1301 and twist 1305 of material may be formed from the tensioning member 315, particularly in those embodiments where the tensioning member 315 comprises a braided member. The individual wires of the braided member can be tied to the body member portion 1303.

The body member portion 1303 provides an additional component, that can have a select material suitable for combining the tensioning member 315 with the arm member 311. Certain embodiments incorporate a body member portion 1303 that improves the bonding between the fastening portion and the arm member 311 by virtue of the material, openings or pores within the body member portion 1303, shape, orientation, and the like. In accordance with a particular embodiment, the body member portion 1303 can include a metal, metal alloy, or polymer material. Suitable metals can include those metals described herein and may particularly include metal alloys including cobalt, chrome, titanium or a combination thereof. Suitable polymer materials can include those biocompatible polymer materials described herein. In accordance with one particular embodiment, the body member portion 1303 can be made of a polyether, such as PEEK.

FIG. 14 includes a cross-sectional illustration of a portion of an implantable device in accordance with an embodiment. In particular, the end member 401 of FIG. 14 is similar to the end member of FIG. 13 including a body member portion 1403 and a fastening portion including a loop 1301 of material and a twist of material 1305. The body member portion 1403 further includes flanges 1407 and 1408 at opposite ends of the body member portion 1403. The flanges 1407 and 1408 are configured to retain the loop 1401 and twist 1405 of material and avoid decoupling from the body member portion 1403.

Figure 15:
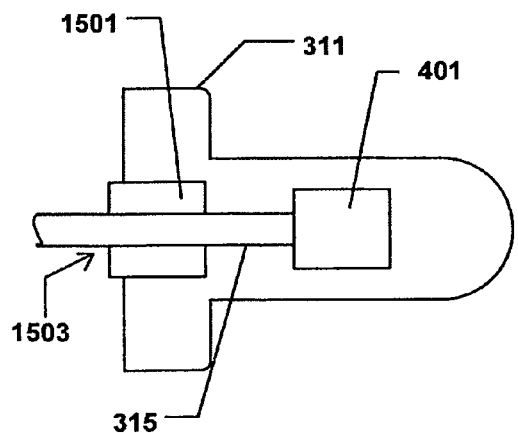
FIG. 15 includes a cross-sectional illustration of a portion of an implantable device in accordance with an embodiment.

Referring to FIG. 15, a cross-sectional illustration of a portion of an implantable device is provided in accordance with an embodiment. In particular, in addition to the end member 401 that is hermetically encased within the arm member 311 and connected to the tensioning member 315, the device further includes a sleeve 1501. The placement and design of the sleeve 1501 is such that it facilitates formation of the device and particularly the positioning of the tensioning member 315 and end member 401 during the forming process, while also reducing the likelihood of decoupling between the tensioning member 315 and the arm member 311. As such, the sleeve 1501 includes an opening 1503 adjacent to an end of the arm member 311 and an interior surface defining a passage extending into the interior of the arm member through which a portion of the tensioning member 315 extends. Moreover, in another certain embodiment, the sleeve 1501 is particularly situated within the arm member 311, such that it is centered along a longitudinal axis, and more particularly the opening 1503 is centered along the longitudinal axis of the arm member 311.

As illustrated, the sleeve 1501 can extend into the interior of the arm member 311, such that at least a portion is hermetically encased and not exposed to the external environment. In accordance with a particular embodiment, a majority of the length of the sleeve 1501 extends into and is encased within the arm member 311 such that it is suitably fixed and bonded to the arm member 311. Notably, a portion of the sleeve 1501 may extend from the first arm member 311, such that it is exterior to the arm member 311 providing a portion for engagement with a machine during formation of the device. In particular embodiments utilizing a sleeve 1501, the portion exterior to the arm member 311 is in direct contact with a compressible member 313.

Still, not greater than about 20% of total length of the sleeve 1501 extends from the arm member 311. In some embodiments the amount of the sleeve 1501 extending from the arm member 311 can be less, such as not greater than about 15%, 10%, or even not greater than about 5% of the total length of the sleeve 1501. According to one particular embodiment, the portion extending is particularly within a range between about 5% and about 20% of the total length of the sleeve.

The sleeve 1501 can include a material that is the same as the material of the arm member 311, or alternatively, in some embodiments, the sleeve 1501 includes a material that is different than the material of the arm member 311. The sleeve 1501 can include a metal or metal alloy, such as those described herein. Other suitable materials can include biocompatible polymers, such as those described herein. In one particular embodiment, the sleeve 1501 includes a polyether material, such as PEEK, or even carbon fiber reinforced PEEK. Still, in accordance with another embodiment, the sleeve 1501 can include a ceramic material. For example, a ceramic material may be used in combination with another material as a reinforcing agent, such as an oxide, carbide, boride, nitride, or any combination thereof.

In accordance with certain other embodiments, the sleeve 1501 is made of a material having a hardness that is less than the hardness of the arm member 311 to avoid localized stresses to the components, which in turn reduces the potential for failure of the device. More particularly, in some embodiments, the sleeve 1501 includes a material having a hardness between that of the tensioning member 315 and the arm member 311, to reduce localized stress to certain components and promote a load sharing design.

Figure 16:
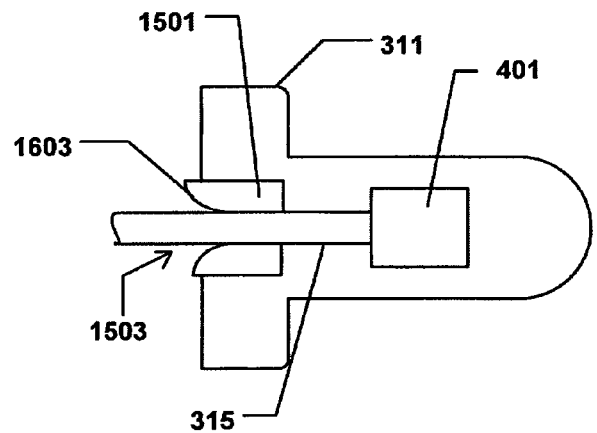
FIG. 16 includes a cross-sectional illustration of a portion of an implantable device in accordance with an embodiment.

FIG. 16 includes a cross-sectional illustration of a portion of an implantable device in accordance with an embodiment. As illustrated, the device includes an end member 401 hermetically encased within the arm member 311 and connected to the tensioning member 315. The device further includes a sleeve 1501 extending into the interior of the arm member 311, such portion being hermetically encased in the arm member 311. In accordance with one embodiment, the sleeve 1501 can have a bearing surface 1603 defining the inner surface in contact with the tensioning member 315. In accordance with a particular embodiment, a portion of the bearing surface can be angled or curved, to remove sharp corners and regions of localized stress.

In accordance with other certain embodiments, the bearing surface 1603 of the sleeve 1501 can include a material that is different than the material of the body of the sleeve 1501. Suitable materials for use as the bearing surface 1603 can include low friction materials. In one embodiment, the bearing surface includes a polymer. Some suitable polymers can include fluoropolymers, for example, polytetrafluoroethylene (PTFE) referred to commercially as Teflon™.

Figure 17:
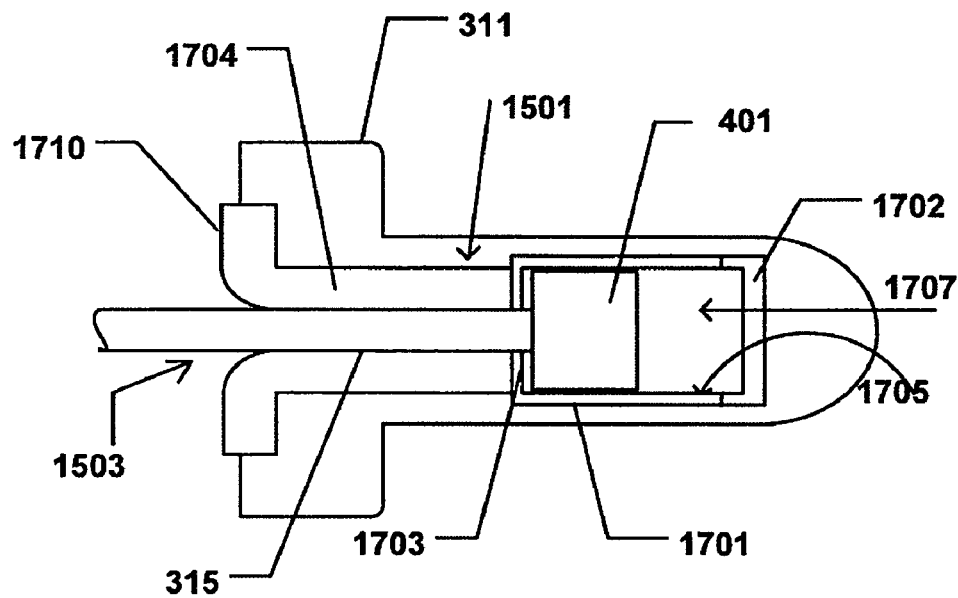
FIG. 17 includes a cross-sectional illustration of a portion of an implantable device in accordance with an embodiment.

FIG. 17 includes a cross-sectional illustration of a portion of an implantable device in accordance with an embodiment. As illustrated, FIG. 17 includes an end member 401 embedded within the interior of an arm member 311 and connected to the tensioning member 315. The device further includes a sleeve 1501 bonded to and extending into the interior of the arm member 311. However, as illustrated, the sleeve 1501 includes multiple components, each of which can be integrally bonded to the arm member 311. In accordance with one embodiment, the sleeve includes a neck portion 1704 which extends from an end of the arm member 311 into the interior of the arm member 311. The sleeve further includes an upper portion 1701 connected to an end of the neck portion 1704 and hermetically encased within the arm member 311, and a cap 1702 connected to an end of the upper portion 1701 and also hermetically encased within the arm member 311.

In accordance with a particular embodiment, the end member 401 is housed within the upper portion 1701 of the sleeve

1501, and a portion of the tensioning member 315 is housed within and substantially surrounded by the neck portion 1704 of the sleeve 1501. The upper portion 1701 has a shape defining an opening within the interior of the arm member 311, and more particularly a translating space 1707 such that the end member 401 can freely translate within the upper portion 1701 of the sleeve 1501. Accordingly, in one particular embodiment, the device includes an end member 401 which is configured to slidably engage within translating space 1707 of the sleeve 1501, such that under certain loads, the end member translates in a direction along the longitudinal axis of the arm member 311. In a more particular embodiment, the upper portion 1701 of the sleeve includes a flange 1703 positioned at an end of the upper portion and configured to abut the end member 401 and restrict the movement of the end member 401 in one direction under certain conditions. Such a design facilitates dynamic transitioning when the device is subject to certain forces as described in more detail herein.

As further illustrated in FIG. 17, the neck portion 1704 of the sleeve includes a flange 1710, which is adjacent to an interface between the arm member 311 and the compressible member (not illustrated). The flange 1710 facilitates positioning of the tensioning member 315 and sleeve 1501 (including all portions) during certain forming processes. Moreover, the flange 1710 increases the surface area of the neck portion 1704 increasing the bond between the neck portion 1704 and the arm member 311 and rigidly fixing the sleeve 1501 within the arm member 311.

Figure 18:
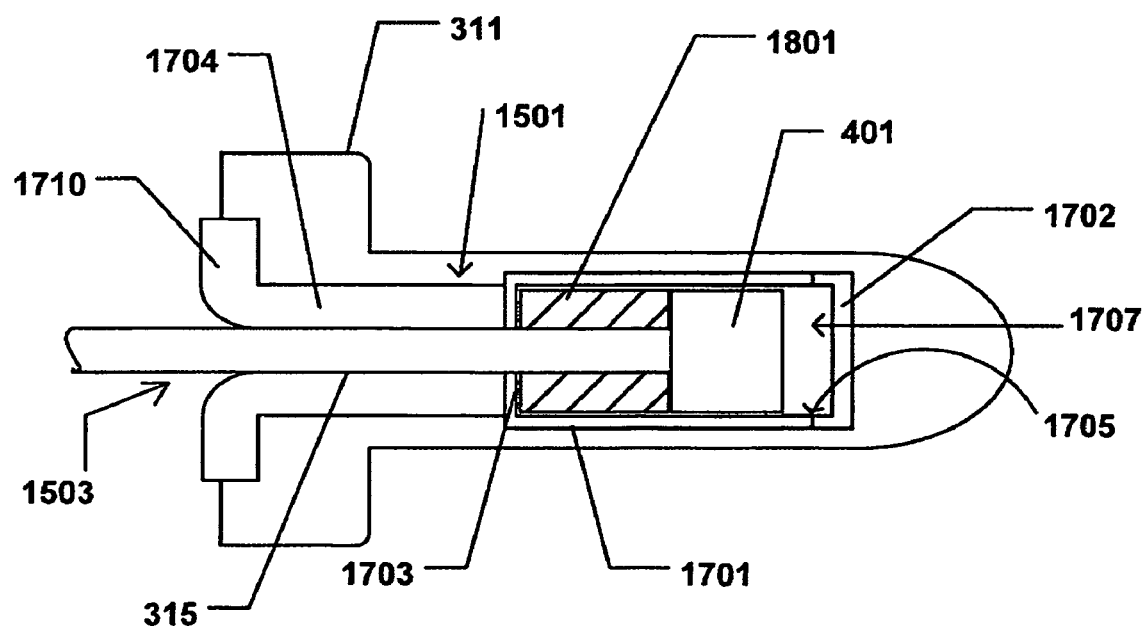
FIG. 18 includes a cross-sectional illustration of a portion of an implantable device in accordance with an embodiment.

FIG. 18 includes a cross-sectional illustration of a portion of an implantable device in accordance with an embodiment. As illustrated, FIG. 18 includes an end member 401 embedded within an arm member 311 and connected to the tensioning member 315. The device includes a sleeve 1501 that can be bonded to and hermetically encased within the interior of the arm member 311. The sleeve 1501 having a neck portion 1704, an upper portion 1701, and a cap 1702, as illustrated in FIG. 17. Additionally, the illustrated embodiment of FIG. 18 includes a biasing member 1801 disposed between the flange 1703 of the upper portion 1701 and a rear surface of the end member 401. The biasing member 1801 can be a sleeve of material that substantially surrounds a portion of the tensioning member 315. In accordance with a particular embodiment, the biasing member 1805 provides additional resilient biasing when the device is under tension. That is, when tension is applied to the device, the end member 401 is urged to move toward the opening 1503 of the sleeve 1501, the biasing member 1801 is positioned within the upper portion 1701 to resist such movement.

As such, the biasing member 1801 can include an organic material, such as a natural organic material, polymer, gel, silicone-based material or a combination thereof. In accordance with a particular embodiment, the biasing member 1801 can include a polymer material. Suitable polymer materials may include biocompatible elastic polymer materials such as an elastomer.

Figure 19:
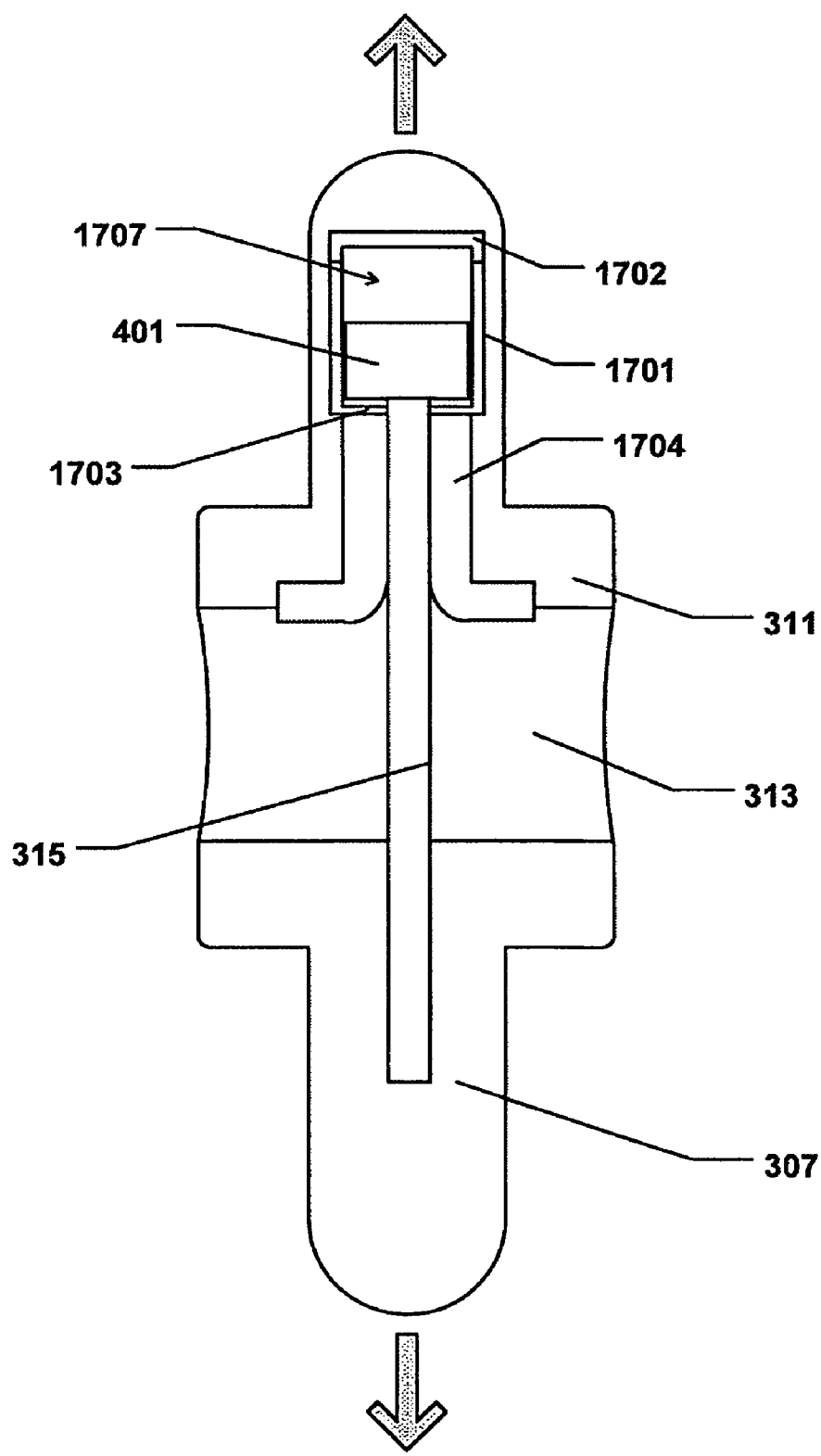
FIG. 19 includes a cross-sectional illustration of an implantable device while in tension in accordance with an embodiment.
Figure 20:
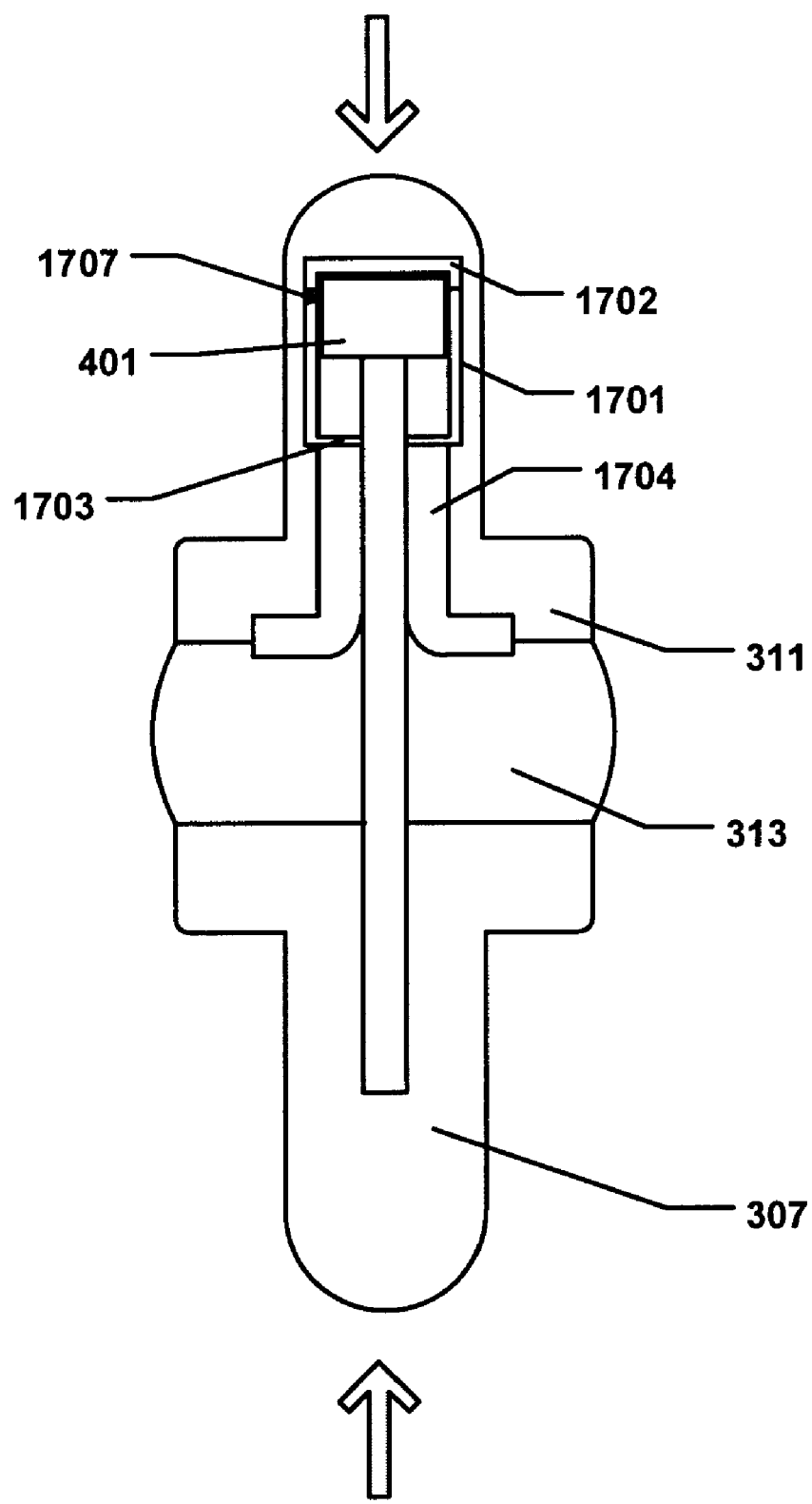
FIG. 20 includes a cross-sectional illustration of the implantable device of FIG. 19 while in compression in accordance with an embodiment.

FIGS. 19 and 20 illustrate the implantable device when subject to different forces, notably a tensioning load (FIG. 19) and a compressive load (FIG. 20). A comparison of FIGS. 19 and 20 demonstrates the different reactions of the components under the different loads and the dynamic transitioning capabilities of the device.

As such, FIG. 19 includes a cross-sectional illustration of an implantable device in accordance with one embodiment while under a tensioning load, wherein the arm members 311 and 307 are pulled in opposite directions (as indicated by the arrows). Such a load may result in deformation of the compressible member 313, however, the tensioning member 315 is designed and positioned such that it manages a majority of the load. Under a tensioning load, the end member 401 abuts the flange 1703 in the upper portion 1701 of the sleeve 1501, fixing the position of the tensioning member 315 relative to the arm members 307 and 311 and providing suitable resiliency against the tensioning load. As will be appreciated, while it is not illustrated, the end members 401 can include any of those as previously described in FIGS. 5-16.

Moreover, the embodiment of FIG. 19 may further include a biasing member within the upper portion 1701 as illustrated in FIG. 18. In such embodiments, the reaction of the end member 401 within the upper portion 1701 is the same, however, the tensioning load is further managed by the biasing member which resists the movement of the end member 401 toward the flange 1703 of the upper portion 1701. Such embodiments may provide additional resistance under tensioning loads, which may be beneficial for certain patients.

FIG. 20 includes a cross-sectional illustration of an implantable device under a compressive load in accordance with an embodiment. As illustrated, under a compressive load, the compressible member 313 absorbs the majority of the compressive load by deflecting (i.e., bowing). Such a design allows the compressible member 313 to maintain and manage the majority of the compressive load while the tensioning member 315 freely translates within the sleeve. Notably, the length of the upper portion, and more particularly the length of the translation space 1707 can be designed such that upon reaching a threshold compressive load that is potentially damaging to the device or patient, the end member 401 can abut the cap 1702 of the upper portion 1701, thus fixing the position of the end member 401 and tensioning member 315 relative to the arm members 307 and 311, providing additional resiliency to the compressive load. Such a design facilitates load sharing between the compressible member 313 and the tensioning member 315.

Figure 21:
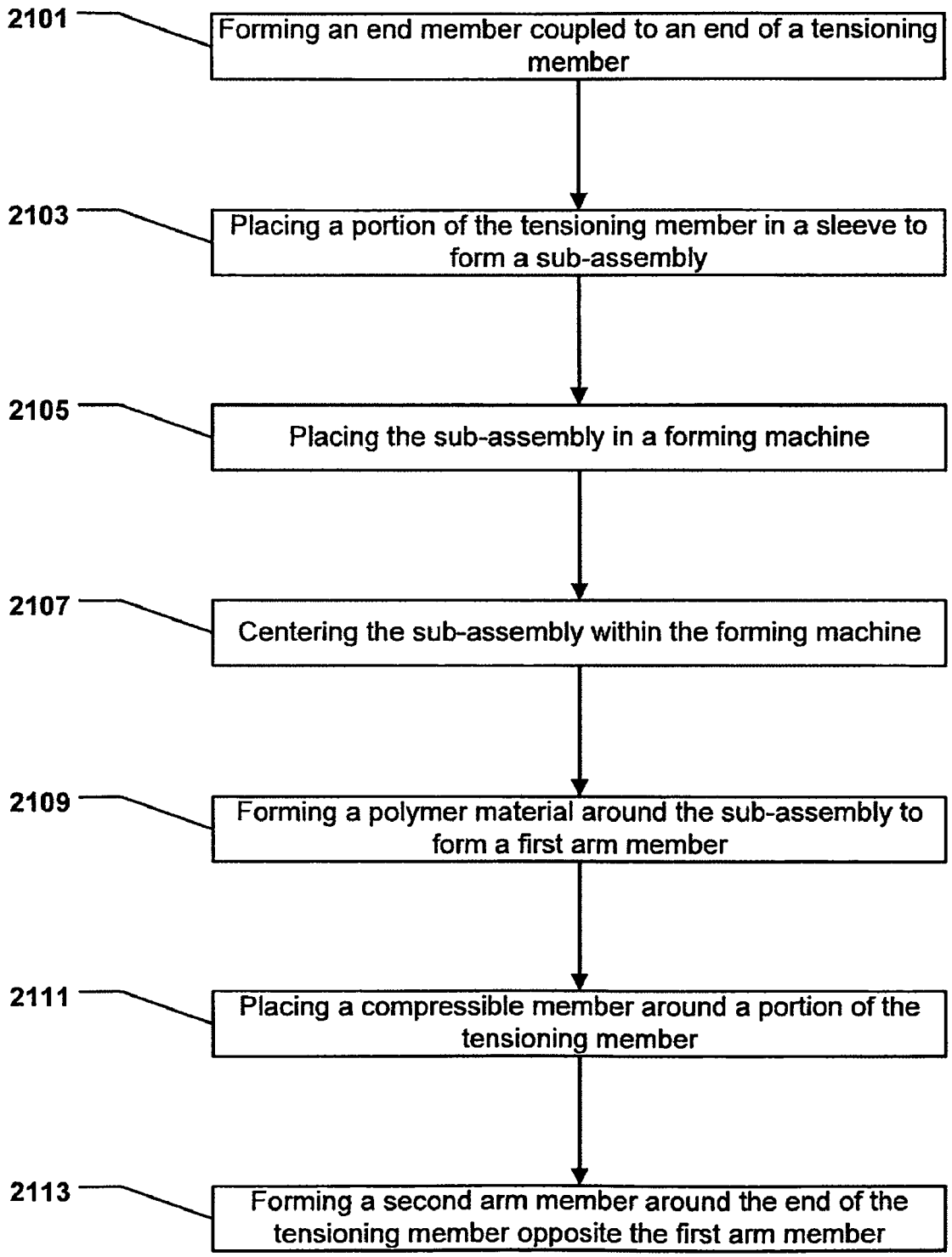
FIG. 21 includes a flow chart illustrating a method of forming an implantable device in accordance with an embodiment.

FIG. 21 includes a flow chart illustrating a method of forming the implantable device in accordance with an embodiment. As illustrated, the forming process is initiated at step 2101 by forming an end member coupled to a tensioning member. The end member can have shapes, materials, and designs of those end members described herein. In accordance with one embodiment, the end member can be formed by manipulating the end of the tensioning member, particularly in embodiments using a tensioning member having a plurality of individual wires, such that the end member forms a knot, braid, loop, twist or combination thereof. In more particular embodiments, manipulation of the end member can include application of heat, pressure, or the like to form a shape out of the end of the tensioning member. For example, in one embodiment the end of the tensioning member can be heated until the material flows and forms a ball of material. Moreover, manipulation can include molding or shaping of the tensioning member to form an end member.

In other embodiments, formation of the end member can include attaching a body member to the tensioning member, such as by use of a coupling connection (e.g., swedging, ferrule, etc), adhesive, pressure, temperature, or a combination thereof.

After forming the end member, the process continues at step 2103 by placing a portion of the tensioning member within a sleeve to form a sub-assembly. The sleeve can have those shapes, materials, and designs described herein. In accordance with embodiments using a sleeve having multiple portions, such as those using a neck portion and upper portion, the tensioning member can be slid through an opening of the neck portion until the end member is suitably seated within an upper portion, and after which, the cap can be connected to the end of the upper portion. In such embodiments, the sub-assembly can include the tensioning member, end member, neck portion, upper portion, and cap. Moreover, in some certain embodiments, the sub-assembly can further include a biasing member included within the upper portion as described herein.

Other embodiments may utilize a simpler sleeve, such as a single component sleeve, and thus the sub-assembly can include the sleeve, tensioning member, and end member. It will be appreciated that in some certain embodiments, a sleeve is not utilized and for such devices, this step may be omitted.

The process of forming the device can continue after forming the sub-assembly at step 2105, which includes placing the sub-assembly within a forming machine. In accordance with one embodiment, the forming machine can be used for a molding process. Some suitable molding processes can include injection molding and compression molding. In one particular embodiment, the forming machine is a compression molding machine used for compression molding polyether materials, such as PEEK.

After placing the sub-assembly within the forming machine, the process continues at step 2107 by centering the sub-assembly within the forming machine. The centering step aids proper positioning of the sub-assembly within the final-formed prosthetic device. In accordance with one embodiment, the centering process is aided by the sleeve, wherein a portion of the sleeve is engaged in the machine to center the sub-assembly within the forming chamber of the machine.

The process of forming the prosthetic device continues at step 2109 by forming a polymer material around the sub-assembly, including the end member and the tensioning member, to form a first arm member. Suitable polymer materials can include those described herein, for example polyurethanes, polyolefins, polyethers, polyesters, and polycarbonates. As described herein, a portion of the sleeve may extend from the first arm member after forming, since this portion of the sleeve is engaged by the machine, and external to the forming chamber. Notably, this step facilitates the formation of an over-molded arm member having the end member and portion of the tensioning member hermetically encased therein and integrally bonded to the arm member.

In accordance with one particular embodiment, the forming process is completed by compression molding PEEK around the sub-assembly. Such a process can include melting the PEEK within a range of temperatures between about 350° C. (660° F.) and about 450° C. (840° F.) allowing the PEEK to flow around the sub-assembly and then pressing the sub-assembly and PEEK to form a portion of the device.

After forming the first arm member at step 2109, the forming process can continue at step 2111 by placing a compressible member around a portion of the tensioning member. In one embodiment, this step can include sliding a compressible member, over the end of the tensioning member opposite the end embedded within the first arm member until the compressible member is abutting the first arm member. In such embodiments, the compressible member can have an opening extending through the longitudinal access for coupling with the tensioning member. In other embodiments, the compressible member may have a slit, such that it is a sleeve, and can be connected to the tensioning member via the slit. The compressible member can be coupled to the first arm member through bonding the compressible member to the first arm member using mechanical coupling means, adhesive, heat, pressure or a combination thereof.

The process of forming the prosthetic device continues at step 2113 by forming a second arm member around the end of the tensioning member opposite the first arm member. Such a process can include the same forming process used to form the first arm member. In accordance with one particular embodiment, prior to forming the second arm member, a second end member can be formed on the end of the tensioning member and configured to be embedded within the second arm member for additional bonding strength between the tensioning member, end member, and second arm member. Certain other embodiments may further utilize a sleeve within the second arm member.

Example

A portion of an implantable device in accordance with embodiments herein was formed according to the following process. A tensioning member made of a titanium alloy material and in a braided form was coupled with an end member, also made of a titanium alloy. A portion of the tensioning member was slid through an opening of a sleeve member. The sleeve member was then coupled to a portion of a compression molding machine (Carber Press, Model 4386) such that a portion of the tensioning member and end member extended into the forming chamber. PEEK material was then loaded into a portion of the press and melted at a temperature of approximately 400° C. (750° F.), until the PEEK material flowed and was compressible. The PEEK material was then pressed and formed around the portion of the tensioning member and end member within the forming chamber. After sufficient cooling, a resulting portion of the implantable device included a sub-assembly including a sleeve, tensioning member, end member, and PEEK arm member was formed.

The present embodiments represent a departure from the state of the art. It is recognized that certain conventional implantable devices, such as those described in U.S. 2006/0264942 and U.S. 2006/0149238, utilize generalized structures having rigid members joined by a compressible member and tensioning member. However, such devices are different in multiple aspects, including among other things, arm members having pre-formed passages for engagement of a tensioning member therein, orientation of the tensioning member within the interior of the arm member, exposure of end members to the environment external to the arm member, and a lack of bonding between the end member and arm member. By contrast, the implantable devices of the embodiments herein include a combination of features not previously recognized in the art, including among other things, end members hermetically encased within the arm members, wherein such end members can be bonded to the material of the arm member, unique shapes, materials, and orientations of such end members, arm members having closed outer surfaces and absent passages extending throughout, sleeves, closed and encased translating spaces, and biasing members. The combination of such features facilitates the formation of implantable devices having improved dynamic transitioning capabilities, and improved resilience to "pull out" of the tensioning member from the arm member.

Additionally, the device incorporates a load sharing design facilitated by the incorporation of multiple components particularly suited to handle particular types of loads, coupled together and particularly oriented so as to provide additional support in situations of excessive forces. As such, while some dynamic coupling elements are known in the art, the present embodiments incorporate a combination of features including design, materials, and positioning of the components that is unrecognized in conventional articles. Additionally, the combination of components facilitate improved processes of forming such devices.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

The Abstract of the Disclosure is provided to comply with 37 C.F.R. §1.72(b) and is submitted with the understanding that it will not be used to interpret or limit the scope or meaning of the claims. In addition, in the foregoing Detailed Description of the Drawings, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all features of any of the disclosed embodiments. Thus, the following claims are incorporated into the Detailed Description of the Drawings, with each claim standing on its own as defining separately claimed subject matter.

What is claimed is:

1. An implantable device comprising:
a first arm member;
a second arm member, wherein the first arm member and the second arm member comprise a first material having a first hardness;
a compressible member disposed between and coupled to the first arm member and the second arm member, wherein the compressible member comprises a second material having- a second hardness less than the first hardness;
a sleeve bonded to the first arm member and extending into an interior of the first arm member, wherein the sleeve has an interior surface defining a passage and a portion of the sleeve is exterior to the first arm member and in direct contact with the compressible member; and
a tensioning member coupled to the first arm member and the second arm member, and a portion of the tensioning member extending through the passage, wherein upon moving the first arm member toward the second arm member the tensioning member translates within the first arm member.

2. The implantable device of claim 1, wherein the tensioning member is fixably connected to the second arm member.

3. The implantable device of claim 1, wherein the tensioning member further comprises an end member coupled to a terminating end of the tensioning member.

4. The implantable device of claim 3, wherein the end member is housed within the sleeve.

5. The implantable device of claim 4, wherein the end member slideably engages an inner surface of the sleeve.

6. The implantable device of claim 1, further comprising a biasing member within the first arm member.

7. The implantable device of claim 6, wherein the biasing member is housed within a portion of the sleeve and is configured to bias an end member coupled to the tensioning member against a surface of the sleeve.

8. The implantable device of claim 1, wherein the first arm member comprises a polymer selected from the group of polymers consisting of, polyurethane, polyolefin, polyether, polyester, and polycarbonate.

9. An implantable device comprising:
a first arm member;
a second arm member wherein the first arm member and the second arm member comprise a first material having- a first hardness;
a compressible member disposed between and coupled to the first arm member and the second arm member, wherein the compressible member comprises a second material having a second hardness less than the first hardness;
a sleeve at least partially positioned within an interior of the first arm member, wherein the sleeve has an opening and a portion of the sleeve is exterior to the first arm member and in direct contact with the compressible member; and
a tensioning member coupled to the second arm member, extending through the compressible member, the opening of the sleeve, and into the interior of the first arm member.

10. The implantable device of claim 9, wherein a majority of the sleeve is embedded within first arm member.

11. The implantable device of claim 9, wherein the sleeve is substantially centered in the first arm member along a longitudinal axis of the first arm member.

12. The implantable device of claim 9, wherein the sleeve comprises a bearing surface.

13. The implantable device of claim 12, wherein a portion of the bearing surface is beveled.

* * * * *